United States Patent [19]
Phan et al.

[11] Patent Number: 5,271,379
[45] Date of Patent: Dec. 21, 1993

[54] ENDOSCOPIC DEVICE ACTUATOR AND METHOD

[75] Inventors: Cu N. Phan; Marshall L. Stoller, both of San Francisco, Calif.

[73] Assignee: The Regents of the University of California, Oakland, Calif.

[21] Appl. No.: 736,175

[22] Filed: Jul. 26, 1991

[51] Int. Cl.$^5$ ............................................. A61B 1/00
[52] U.S. Cl. ........................................... 128/4; 606/1
[58] Field of Search ............ 128/4, DIG. 1; 251/295; 604/182, 38; 433/101; 606/1

[56] References Cited

U.S. PATENT DOCUMENTS

| | | | |
|---|---|---|---|
| 3,272,393 | 9/1966 | Roeser | 251/295 |
| 3,476,153 | 11/1969 | Roland | 251/295 |
| 3,594,829 | 7/1971 | Seek | 251/295 |
| 3,834,392 | 9/1974 | Lampman et al. | 128/4 X |
| 4,122,853 | 10/1978 | Smith | 606/11 X |
| 4,517,963 | 5/1985 | Michel | 128/6 |
| 4,616,632 | 10/1986 | Wigoda | 128/20 |
| 4,708,125 | 11/1987 | Miketi et al. | 128/4 |
| 4,854,301 | 8/1989 | Nakajima | 128/4 |
| 4,862,886 | 9/1989 | Clarke et al. | 606/7 |
| 4,998,972 | 3/1991 | Chin et al. | 128/6 |
| 5,167,220 | 12/1992 | Brown | 128/4 |

OTHER PUBLICATIONS

Hand, Roy H., M.D., *Dis Colon Rectum*, May 1991, pp. 419–420.

Mauermayer, W. *Transurethral Surgery*, 1983, pp. 33–34, Springer-Verlag, Berlin Heidelberg, New York.

*Primary Examiner*—Richard J. Apley
*Assistant Examiner*—Karen A. Jalbert
*Attorney, Agent, or Firm*—Townsend and Townsend Khourie and Crew

[57] ABSTRACT

An actuator (2) is used for actuating an auxiliary endoscopic device, such as an irrigation syringe (4), a pronged forcep (98) or a flexible stone-capturing basket (86). The auxiliary endoscopic device has a stationary portion (46) and a portion (62) which moves relative to the stationary portion. The actuator includes a foot pedal assembly (6) having a movable part (14) and a stationary part (12), a housing (8) and a coaxial cable (10). The coaxial cable includes an inner wire (30) and an outer tube (22) fixed at its ends (24, 26) to the movable part of the foot pedal assembly and to the housing. The stationary portion of the auxiliary endoscopic device is secured to the housing while the movable portion is connected to one end of the wire, the other end of the wire being connected to the stationary part of the foot pedal assembly. Accordingly, moving the movable part of the foot pedal assembly, typically by the operator's foot, thigh or elbow, causes the wire to slide back and forth within the elongate tube, thus moving the movable portion of the auxiliary device relative to the stationary portion. This allows the auxiliary endoscopic device to be actuated using one's foot to free up both of the user's hands to operate the endoscope.

14 Claims, 4 Drawing Sheets

ENDOSCOPIC DEVICE ACTUATOR AND METHOD

BACKGROUND OF THE INVENTION

Endoscopes are used by physicians to visually examine the interior of a bodily canal or hollow organ. Endoscopic procedures require a comfortable operator in a darkened room. Vision is limited, especially with miniaturized instrumentation, due to small irrigation ports with high resistance, air bubbles with refractive distortion, and varying amounts of debris in the operative field ranging from blood to stone particles. Offset lenses allow some mobility when the endoscope is torqued. However, the operator must remain focused to successfully achieve his or her goal. Shifting one's visual attention from the endoscopic field to operate an auxiliary device, such as an irrigation syringe, flexible basket or pronged forceps, hinders the completion of a successful procedure due to various factors; these factors include the time required for the operator's eyes to adjust to different light conditions, the time required to reorient the operative field, and the time required to eliminate air bubbles and/or blood clots. Frequently, the operator requires an assistant to operate the accessories, as two hands are required to effectively control the endoscope. Communication with the assistants is suboptimal; an assistant cannot maneuver such auxiliary endoscopic devices as the operator ideally would. For example, three-pronged forceps are often opened too far or not far enough; the finesse needed in endoscopic manipulation is simply not generally achieved when assistants are controlling the auxiliary devices.

SUMMARY OF THE INVENTION

The present invention is directed to an actuator which allows the operator of an endoscope to control the movement of an auxiliary endoscopic device using one or more parts of the operator's body other than the operator's hands, such as a foot, a thigh or an elbow. Doing so leaves both of the operator's hands free to control the endoscope.

The actuator is used to actuate auxiliary endoscopic devices, such as irrigation syringes, pronged forceps or flexible stone-capturing baskets. Each auxiliary endoscopic device has a relatively stationary portion and a portion which moves relative to the stationary portion. The actuator typically includes a pedal, a housing and, in a preferred embodiment, a coaxial cable connecting the two. The coaxial cable includes an outer, elongate tube, fixed at either end to the foot pedal and to the housing, and an inner wire. The stationary portion of the auxiliary endoscopic device is secured to the housing while the movable portion is connected to one end of the wire. The other end of the wire is connected to the pedal. Accordingly, moving the pedal, typically by the operator's foot, thigh or elbow, causes the wire to slide back and forth within the elongate tube, thus moving the movable portion of the auxiliary device relative to the stationary portion. This allows the auxiliary endoscopic device to be actuated by the operator while freeing up the operator's hands to operate the endoscope.

One of the main features of the invention is the recognition that the operator of an endoscope may be able to control the physical movement of an auxiliary endoscopic device using a body part other than one's hands, such as his or her foot, thigh or elbow. Doing so frees up the operator's hands to continue operating the endoscope while maintaining the operator's own control over the physical manipulation of the auxiliary endoscopic device. The need to provide instructions to and rely on assistants to operate auxiliary endoscopic devices can thus be minimized or eliminated.

The present invention is preferably carried out using mechanical or hydraulic connections between a foot pedal assembly and the housing of the actuator. In either event, an elongated tube carries the wire or hydraulic fluid and also acts as a physical constraint to the housing. However, in appropriate circumstances, the operable connection between the foot pedal assembly and the housing could be electrical as well.

In this patent application, certain elements are described as being movable while associated elements are described as being stationary. These are relative terms and are not meant in an absolute sense.

Other features and advantages of the invention will appear from the following description in which the preferred embodiments have been set forth in detail in conjunction with the accompanying drawings.

DESCRIPTION OF THE PREFERRED EMBODIMENTS

Figure 1:
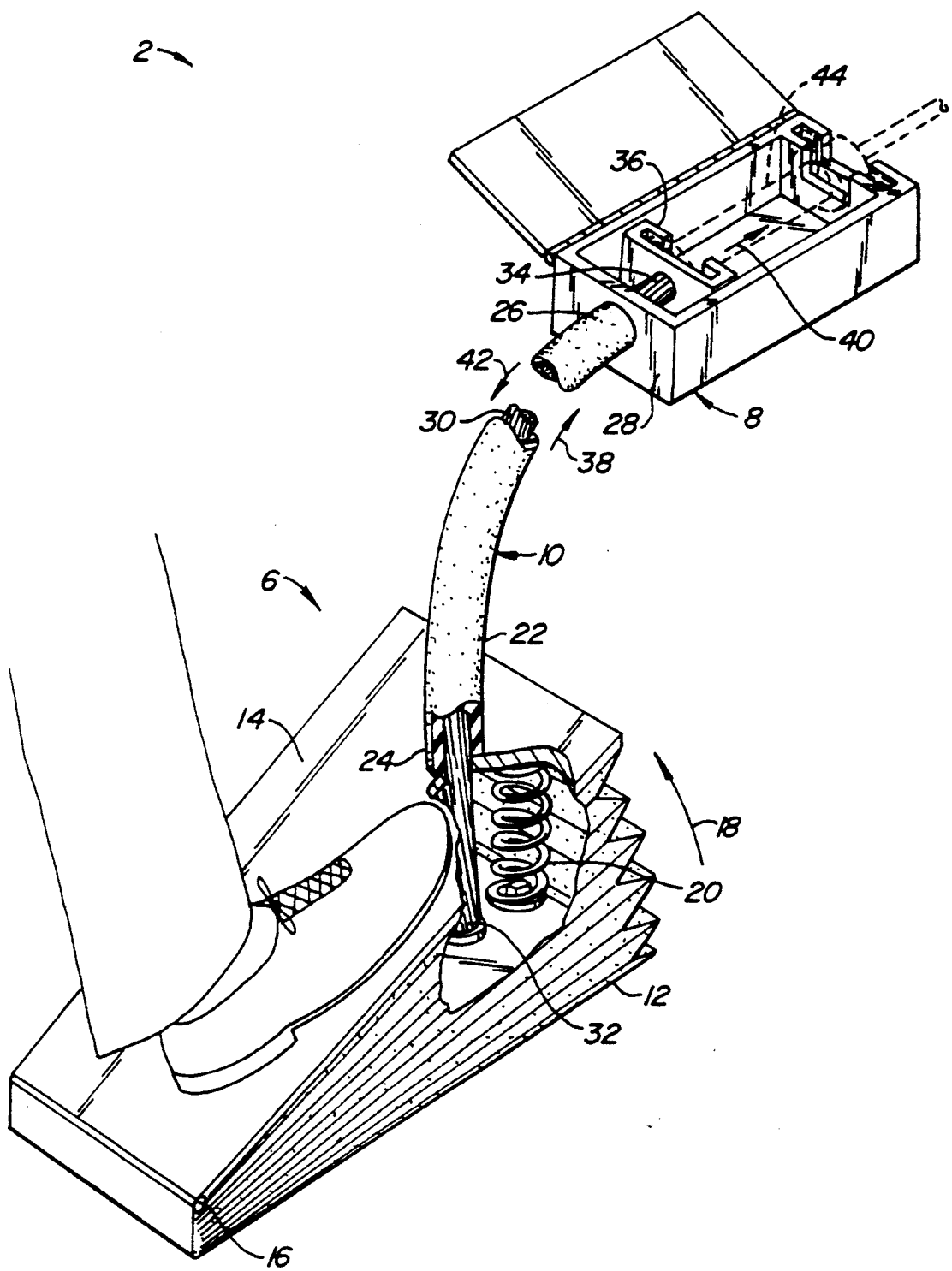
FIG. 1 is an overall view of a foot-operated actuator made according to the invention.
Figure 2:
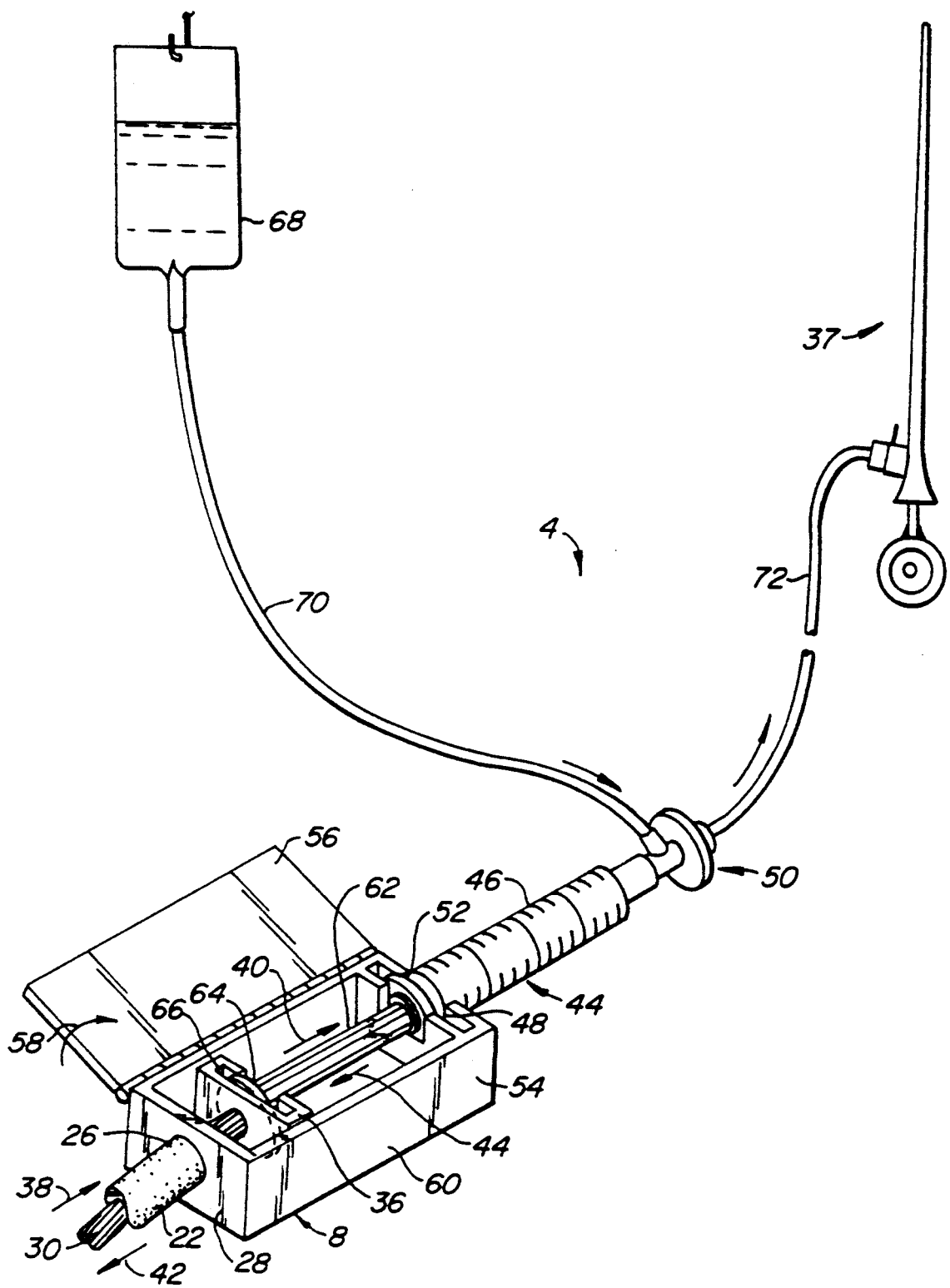
FIG. 2 shows a portion of the actuator of FIG. 1 in use with an irrigation syringe.

FIGS. 1 and 2 illustrate a foot-operated actuator 2 adapted for use with an irrigation syringe assembly 4, assembly 4 being a type of auxiliary endoscopic device. Actuator 2 includes a foot pedal assembly 6 and a housing 8 coupled by a coaxial cable 10. Foot pedal assembly 6 includes a relatively stationary base 12 connected to a movable foot support 14 by pivot 16. Foot support 14 is biased upwardly, that is in the direction of arrow 18 by a coil spring 20.

Coaxial cable 10 includes an outer, hollow elongate tube 22 having a first end 24 secured to foot support 14 and a second end 26 secured to one end 28 of housing 8. Coaxial cable 10 also includes a center wire 30 which passes through and is longer than coaxial cable 10. Wire 30 is flexible but relatively resistant to buckling under axial compression. Coaxial cable 10 could be of the type used as bicycle brake cable. Wire 30 has a proximal end 32 secured to base 12 and a distal end 34 secured to a syringe plunger adapter 36 mounted within housing 8. When the operator of an endoscope 37 presses on foot support 14, foot support 14 moves in the direction opposite arrow 18, causing wire 30 to move within tube 22 in the direction of arrow 38, thus moving adapter 36 in the direction of arrow 40. Releasing foot support 14 allows the foot support 14 to move, due to spring 20, in the direction of arrow 18, thus causing wire 30 and adapter 36 to move in directions of arrows 42, 44 respectively.

Syringe assembly 4 is of conventional design. Assembly 4 includes a syringe 44 having a barrel 46 with a radially outwardly extending finger ledge 48 at one end and a one-way valve assembly 50 at the other. Finger ledge 48 fits within a cutout 52 formed at a second end 54 of housing 8. Housing 8 and cutout 52 are sized to securely capture finger ledge 48 within cutout 52 when the lid 56 of housing 8 is pivoted in the direction of arrow 58 onto the body 60 of the housing. An appropriate catch, not shown, may be used to keep lid 56 closed. Syringe 44 also includes a plunger 62 having a radially enlarged end 64 which fits within an appropriately sized slot 66 formed in adapter 36. Thus, as adapter 36 moves in the direction of arrow 44, plunger 62 likewise moves, causing liquid within I.V. bag 68, such as a sterile saline solution, to be pulled through tube 70 and into barrel 46. On movement of plunger 62 in the direction of arrow 40, the liquid in barrel 46 is expulsed through valve assembly 50, through tube 72 and through endoscope 37. Thus, the operator of the endoscope can control the operation of irrigation syringe assembly 4 using his or her foot. There is no need to remove one or both of the user's hands from the endoscope to do so, thus enhancing performance.

Figure 3:
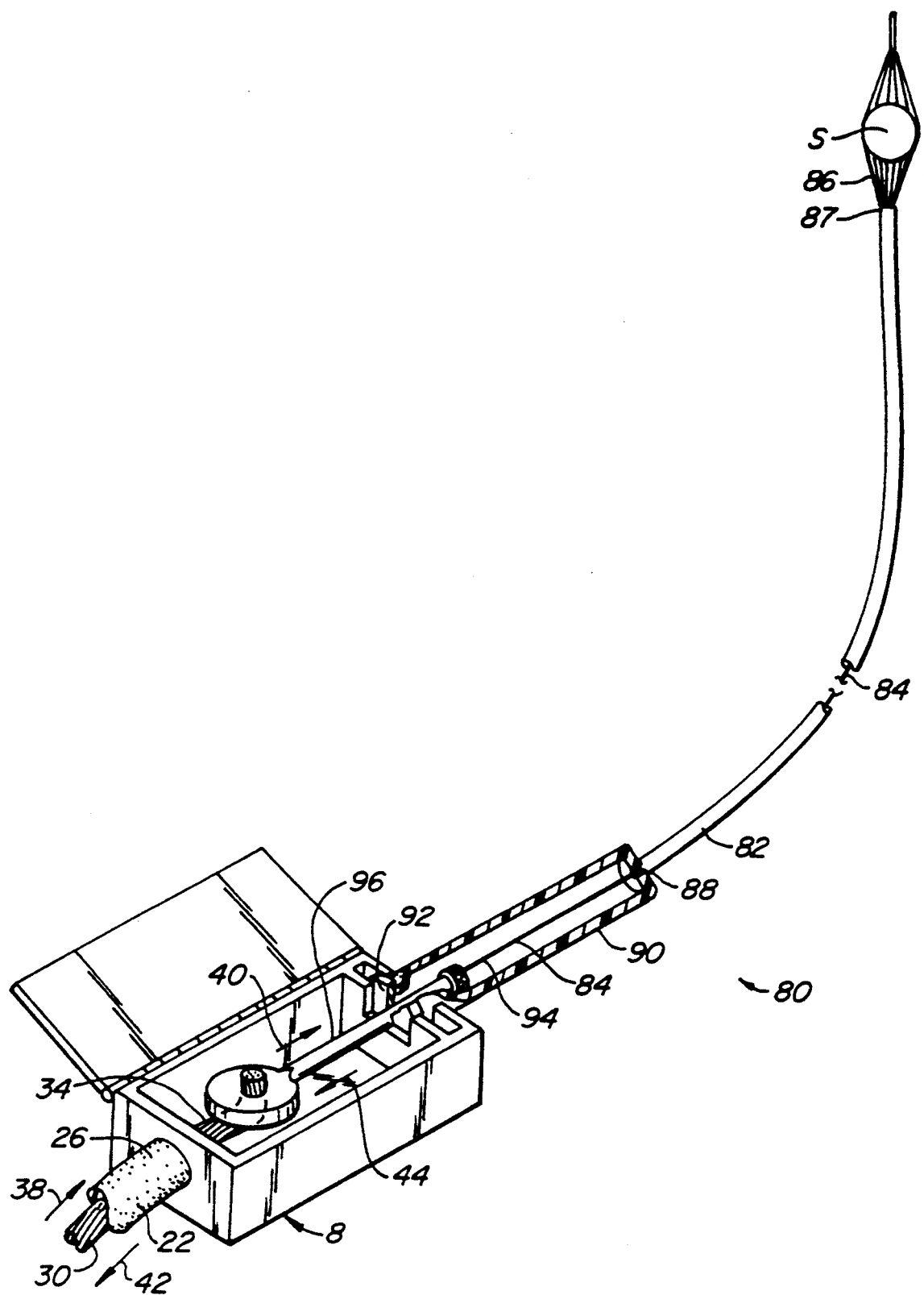
FIG. 3 illustrates a portion of the foot-operated actuator of FIG. 1 adapted for use with a basket-type auxiliary endoscopic device.

Other types of auxiliary endoscopic devices can be used with the invention as well. FIG. 3 illustrates container 8 connected to a basket-type auxiliary endoscopic device 80. Device 80 includes an outer sheath 82 through which an inner wire 84 freely passes. Wire 84 is connected at its distal end 87 to a conventional expandable and contractible basket 86 shown in FIG. 3 holding a kidney stone S. The proximal end 88 of sheath 82 is secured to an adaptor 90. Adaptor 90 has an enlarged end 92 which fits within cutout 52 at second end 54 of housing 8. The proximal end 94 of wire 84 is connected to distal end 34 of wire 30 by a connecting link 96. Thus, movement of link 96 in the direction of arrows 40, 44 causes basket 86 to open and close as desired by the operator.

Figure 4:
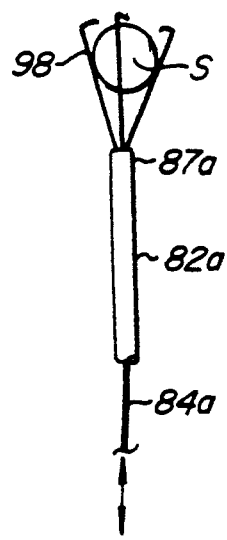
FIG. 4 illustrates a portion of a three-pronged forcep device which could be used in lieu of the basket-type auxiliary endoscopic device of FIG. 3.

FIG. 4 illustrates a pronged forcep 98 mounted to the distal end 87a of wire 84a, wire 84a passing through a sheath 82a as with device 80. Pronged forcep 98 is controlled the same way as basket 86 of device 80 and is thus not described in detail.

Figure 5:
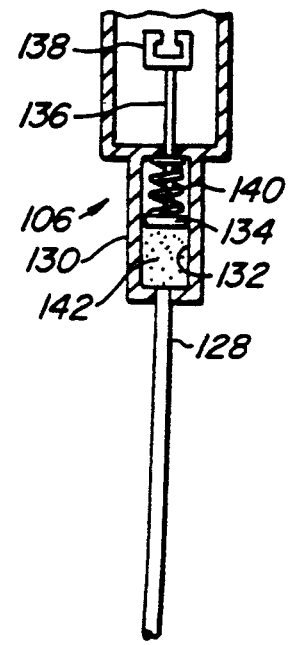
FIG. 5 is an overall view of an alternative embodiment of the actuator of FIG. 1 using hydraulic pump.
Figure 5:
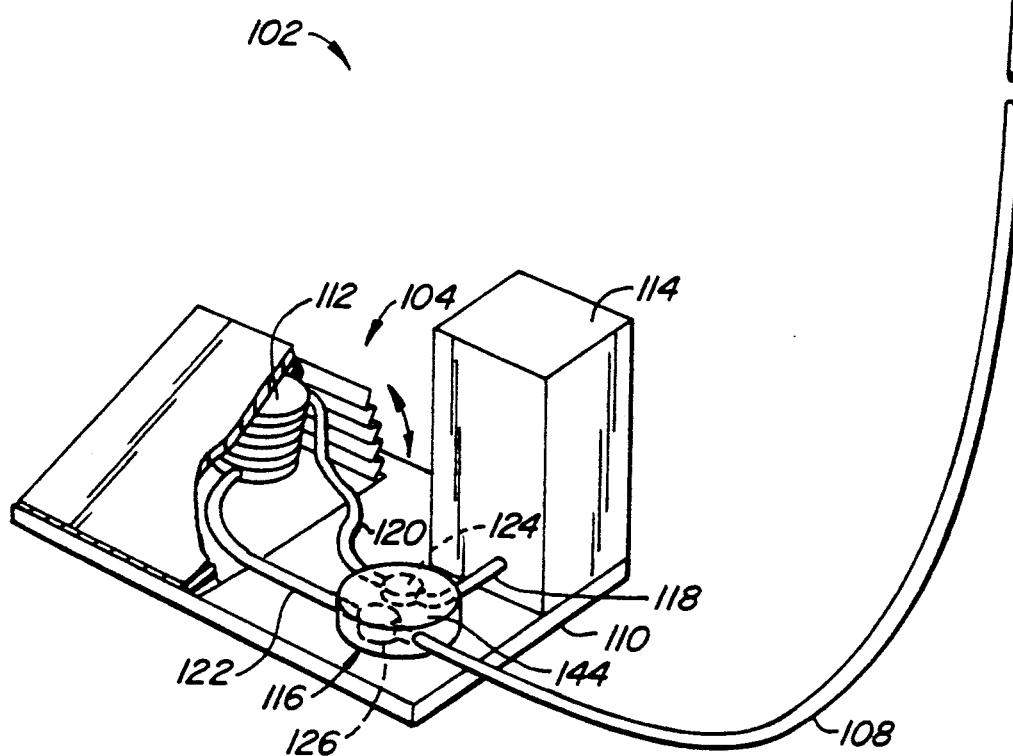

FIG. 5 illustrates an overall view of an alternative embodiment of a foot operated actuator 2 of FIG. 1. Actuator 102 includes a foot-operated pump assembly 104 coupled to a hydraulic working assembly 106 by a flexible tube 108. Pump assembly 104 includes a base 110 on which a foot actuated bellows 112, a reservoir 114 and a valve assembly 116 are mounted. Reservoir 114 is fluidly connected to bellows 112 through valve assembly 116 by lines 118, 120. Bellows 112 is fluidly connected to tube 108, also through valve assembly 116, by a line 122. Valve assembly 116 includes first and second check valves 124, 126 which couple line 118 to line 120 and line 122 to line 108, respectively. Check valves 124, 126 normally permit fluid flow only from line 118 to line 120 and from line 122 to line 108. Therefore, collapse and release of bellows 112, which is biased to a normally open or expanded condition, will cause fluid from reservoir 114 to pass through line 118, check valve 124, line 120 and into bellows 112. Compressing bellows 112 causes hydraulic fluid to pass through line 122, through check valve 126 and into tube 108.

The distal end 128 of tube 108 is connected to working assembly 106. Working assembly 106 includes a body 130 defining a cylindrical bore 132 within which a piston 134 and plunger 136 move. Plunger 136 has an outer end 138 used to drive the moveable portion of an auxiliary endoscopic device, such as end 64 of plunger 62 shown in FIG. 2. Piston 134 is biased by spring 140 which tends to force hydraulic fluid 142 within bore 132 back through tube 108. This can occur, however, only when check valves 124, 126 have been effectively neutralized. In the preferred embodiment, check valves 124, 126 are constructed so that pressing on the top 144 of check valve assembly 116 effectively neutralizes check valves 124, 126 permitting hydraulic fluid 142 to flow back-through tube 122, bellows 112, tube 120, Valve 124, tube 118 and into reservoir 114. Other valve arrangements, such as foot actuated bypass valves, could be used to permit hydraulic fluid to pass back into reservoir 114.

Modifications and variations can be made to the disclosed embodiments without departing from the subject of the invention as defined in the following claims. For example, instead of putting spring 20 between base 12 and foot support 14, a spring could be positioned between second end 54 of housing 8 and plunger adapter 36. A foot strap, not shown, could be used on foot support 14 to permit the user to raise and lower the foot support to eliminate the need for spring 20. Actuator 2 could be electrical in nature with the foot pedal assembly controlling the operation of, for example, a stepper motor mounted within the housing and driving, for example, an appropriate worm and worm gear drive. Housing 8 need not be an enclosure but could be simply a base to which, for example, hollow tube 22 and finger ledge 48 of syringe 44 are secured. Foot pedal assembly 6 could be constructed so that end 24 of tube 22 does not move but rather end 32 of wire 30 would be driven up and down to cause wire 30 to move within tube 22.

What is claimed is:

1. An actuator for actuating an auxiliary endoscopic device using a body part of an operator of an endoscope, the endoscope having a passageway adapted to receive the auxiliary endoscopic device, the body part being other than the operator's hands, the auxiliary device of the type including a relatively stationary outer sheath having first and second ends and a movable portion housed for axial movement within the outer sheath, the actuator comprising:
   a body part actuated assembly including a body part actuable movable part and a stationary part;
   a housing adapted to receive the first end of the outer sheath;
   an elongate tube secured to the housing at one end and to a selected one of the movable end stationary parts of the body part actuated assembly at the other end;
   a wire substantially housed with the elongate tube and having a proximal end and a distal end, the wire being connected to an other one of the movable and stationary parts of the body part actuated assembly at the proximal end; and
   means for coupling the distal end of the wire to the movable portion of the auxiliary device when the housing receives the outer sheath of the auxiliary device so that an axial displacement of the wire within the elongate tube causes the movable portion to move.

2. The actuator of claim 1 further comprising means for biasing the movable part of the body part actuated assembly to a first position.

3. The actuator of claim 2 wherein the biasing means includes a spring captured between the movable and stationary parts of the body part actuated assembly.

4. The actuator of claim 1 further comprising means for connecting the movable part of the body part actuated assembly to the housing.

5. The actuator of claim 1 wherein the movable part of the body part actuated assembly includes a foot pedal element.

6. An actuator for actuating an auxiliary endoscopic device using a body part of an operator of an endoscope, the endoscope having a passageway adapted to receive the auxiliary endoscopic device, the body part being other than the operator's hands, the auxiliary device of the type including a relatively stationary outer sheath having first and second ends and a movable portion housed for axial movement within the outer sheath, the actuator comprising:

a housing adapted to receive the first end of the outer sheath and including a fluid chamber, a piston within the fluid chamber, and an outer end coupled to the piston and being adapted to be coupled to the movable portion of the auxiliary device;

a hydraulic pump assembly including a movable, body part actuated pump part, a hydraulic pump coupled to and driven by the pump part, the hydraulic pump assembly and the housing fluidly coupled by an elongate tube, the hydraulic pump having an exit fluidly coupled to the tube and an entrance fluidly coupled to a reservoir, so that actuating the pump part causes liquid to be pumped from the hydraulic pump into the tube so to pressurize the fluid chamber and apply a force to the piston.

7. A method for aiding an operator of an endoscope having a passageway adapted to receive an auxiliary endoscopic device, said method aiding control of the auxiliary endoscopic device during an endoscopic procedure, the auxiliary device having a relatively stationary outer sheath with first and second ends and a movable portion housed for axial movement within the outer sheath, the method comprising the following steps:

providing a body part actuated assembly including a movable part and a stationary part, a housing adapted to receive the first end of the outer sheath, an elongate tube secured to the housing at one end and to a selected one of the movable and stationary parts of the body part actuated assembly at the other end, a wire substantially housed within the elongate tube and having a proximal end and a distal end, the wire being connected to an other one of the movable and stationary parts of the body part actuated assembly at the proximal end, and means for coupling the distal end of the wire to the movable portion of the auxiliary device when the housing receives the outer sheath of the auxiliary device so that an axial displacement of the wire within the elongate tube causes the movable portion to move;

manipulating the endoscope using the operator's hands; and actuating the pedal suing the operator's body part thereby axially moving the movable portion of the auxiliary device within the outer sheath without the need to use the operator's hands.

8. A method for aiding an operator of an endoscope having a passageway adapted to receive an auxiliary endoscopic device, said method aiding control of the auxiliary endoscopic device during an endoscopic procedure, the auxiliary device having a relatively stationary outer sheath with first and second ends and a movable portion housed for axial movement within the outer sheath, the method comprising the following steps:

providing a body part operated actuator including a pedal in a region near a body part of the operator, other than the operator's hands, the pedal being actuated by the operator's body part, and means for operatingly coupling the movable portion of the auxiliary device to the pedal, the pedal including first and second parts, the first part being movable relative to the second part;

manipulating the endoscope using the operator's hands; and actuating the pedal using the operator's body part thereby axially moving the movable portion of the auxiliary device within the outer sheath without the need to use the operator's hand;

providing the body part operated actuator with a housing spaced apart from the pedal, the pedal including a movable part and a stationary part;

connecting the pedal to the housing by a coaxial cable having an inner cable and an outer sheath, the movable part being secured to the outer sheath and the inner cable being coupled to the stationary part;

scouring the outer sheath of the coaxial cable to the housing; and coupling the inner cable to the movable portion of the auxiliary device;

9. An actuator for actuating an endoscopic irrigation assembly using a body part of an operator of an endoscope, the endoscope having a fluid passageway adapted to receive a fluid from the irrigation assembly, the body part being other than the operator's hands, the irrigation assembly of the type including a fluid supply, a fluid conduit coupling the fluid supply to the fluid passageway and a fluid pumping device coupled to the fluid conduit, the fluid pumping device including a relatively stationary portion and a movable portion, the fluid pumping device configured so that moving the movable portion relative to the relatively stationary portion causes fluid to flow from the fluid source, through the fluid conduit and to the fluid passageway, the actuator comprising:

a body part actuated assembly including a movable part and a stationary part;

a housing adapted to receive the first end of the outer sheath;

an elongate tube secured to the housing at one end and to a selected one of the movable and stationary parts of the body part actuated assembly at the outer end;

a wire substantially housed within the elongate tube and having a proximal end and a distal end, the wire being connected to an other one of the movable and stationary parts of the body part actuated assembly at the proximal end; and means for coupling the distal end of the wire to the movable portion of the auxiliary device when the housing receives the outer sheath of the auxiliary device so that an axial displacement of the wire within the elongate tube causes the movable portion to move.

10. The actuator of claim 9 further comparing means for biasing the movable part of the body part actuated assembly to a first position.

11. The actuator of claim 10 wherein the biasing means includes a spring captured between the movable and stationary parts of the body part actuated assembly.

12. The actuator of claim 9 further comprising means for connecting the movable part of the body part actuated assembly to the housing.

13. The method for controlling an irrigation assembly during an endoscopic procedure, the endoscope having a passageway adapted for fluid coupling with the endoscope irrigation assembly, the irrigation assembly having a movable portion movable relative to a relatively stationary portion, the method comprising the following steps:

provating a housing adapted to receive the first end of the outer sheath and including a fluid chamber, a piston within the fluid chamber, and an outer end coupled to the piston and being adapted to be coupled to the movable portion of the auxiliary device, a hydraulic pump assembly including a movable, body part actuated pump art, a hydraulic pump coupled to an driven by the pump part, the hydraulic pump assembly and the housing fluidly coupled by an elongate tube, the hydraulic pump having an exit fluidly coupled to the tube and an entrance fluidly coupled to a reservoir, so that actuating the pump part causes liquid to be pumped from the hydraulic pump into the tube so to pressurize the fluid chamber and apply a force to the piston, t he piston being adapted to be coupled to the movable portion of the irrigation system so that displacement of the piston causes displacement of the movable portion;

establishing fluid coupling of the irrigation assembly to the passageway in the endoscope;

manipulating the endoscope using the operator's hands; and actuating the pedal using the operator's body part thereby moving the movable portion of the irrigation assembly without the need to use the operator's hands.

14. The method of claim 13 further comprising the steps of:

providing the body part actuated pump part with a pedal.

* * * * *